(12) United States Patent
Pinchera et al.

(10) Patent No.: US 9,468,619 B2
(45) Date of Patent: Oct. 18, 2016

(54) 3,5,3'-TRIIODOTHYRONINE SULFATE AS THYROMIMETIC AGENT AND PHARMACEUTICAL FORMULATIONS THEREOF

(71) Applicant: BRACCO S.P.A., Milan (IT)

(72) Inventors: Aldo Pinchera, Pisa (IT); Livio Cavalieri, Milan (IT); Federico Maisano, Lodi (IT); Giovanni Rivolta, Monza (IT); Ferruccio Santini, Carrara (IT); Fulvia Vella, Monza (IT)

(73) Assignee: Bracco S.P.A., Milan (IT)

( * ) Notice: Subject to any disclaimer, the term of this patent is extended or adjusted under 35 U.S.C. 154(b) by 428 days.

(21) Appl. No.: 13/916,710

(22) Filed: Jun. 13, 2013

(65) Prior Publication Data

US 2013/0281536 A1 Oct. 24, 2013

Related U.S. Application Data

(63) Continuation of application No. 13/083,047, filed on Apr. 8, 2011, now abandoned.

(51) Int. Cl.
*A61K 31/198* (2006.01)
*A61K 31/197* (2006.01)
*A61K 9/20* (2006.01)
*G01N 21/76* (2006.01)
*G01N 33/561* (2006.01)
*A61K 31/28* (2006.01)

(52) U.S. Cl.
CPC .............. *A61K 31/197* (2013.01); *A61K 9/20* (2013.01); *A61K 31/198* (2013.01); *A61K 31/28* (2013.01); *G01N 21/76* (2013.01); *G01N 33/561* (2013.01)

(58) Field of Classification Search
CPC .. A61K 31/197; A61K 31/198; A61K 31/28; A61K 9/20
See application file for complete search history.

(56) References Cited

U.S. PATENT DOCUMENTS

| | | | |
|---|---|---|---|
| 2,970,165 A | 1/1961 | Raymond et al. |
| 2,993,928 A | 7/1961 | Razdan et al. |
| 3,313,839 A | 4/1967 | Rozzi |
| 4,254,095 A | 3/1981 | Fisher et al. |
| 5,116,828 A | 5/1992 | Miura et al. |
| 5,158,978 A | 10/1992 | Rubin |
| 5,225,204 A | 7/1993 | Chen et al. |
| 5,272,078 A | 12/1993 | Larsen et al. |
| 5,324,522 A | 6/1994 | Krenning et al. |
| 5,753,254 A | 5/1998 | Khan et al. |
| 5,955,105 A | 9/1999 | Mitra et al. |
| 5,958,979 A | 9/1999 | Lahr et al. |
| 6,056,975 A | 5/2000 | Mitra et al. |
| 6,406,667 B1 | 6/2002 | Singh et al. |
| 6,555,581 B1 | 4/2003 | Franz et al. |
| 6,599,942 B1 | 7/2003 | Kukkola |
| 6,646,007 B1 | 11/2003 | Schreder et al. |
| 6,740,680 B1 | 5/2004 | Danforth, Jr. et al. |
| 6,855,333 B1 | 2/2005 | Spireas |
| 6,979,462 B1 | 12/2005 | Spireas |
| 7,052,717 B2 | 5/2006 | Hanshew et al. |
| 7,067,148 B2 | 6/2006 | Franz et al. |
| 7,101,569 B2 | 9/2006 | Franz et al. |
| 7,163,918 B2 | 1/2007 | Piccariello et al. |
| 7,691,411 B2 | 4/2010 | Di Martino et al. |
| 7,723,390 B2 | 5/2010 | Garavani et al. |
| 8,008,349 B2 | 8/2011 | Schreder et al. |
| 2001/0051657 A1 | 12/2001 | Chiang |
| 2002/0076827 A1 | 6/2002 | Salhanick et al. |
| 2003/0050344 A1 | 3/2003 | Garavani et al. |
| 2003/0198668 A1* | 10/2003 | Franz ................... A61K 31/198 424/465 |
| 2004/0063611 A1 | 4/2004 | Schreder et al. |
| 2004/0156893 A1 | 8/2004 | Klein et al. |
| 2005/0249801 A1 | 11/2005 | Spireas |
| 2005/0266570 A1 | 12/2005 | Carey et al. |
| 2005/0272816 A1 | 12/2005 | Pinchera et al. |
| 2007/0014851 A1 | 1/2007 | Burghart et al. |
| 2007/0276042 A1* | 11/2007 | Gant ....................... C07C 57/30 514/569 |
| 2008/0003284 A1 | 1/2008 | Franz et al. |
| 2008/0193527 A1* | 8/2008 | Ruiz Amenos ...... A61K 9/1652 424/465 |
| 2010/0136109 A1 | 6/2010 | Ross et al. |
| 2011/0064773 A1 | 3/2011 | Leverve et al. |
| 2011/0245342 A1 | 10/2011 | Pinchera et al. |

FOREIGN PATENT DOCUMENTS

| | | |
|---|---|---|
| CA | 2333193 A1 | 11/1999 |
| CA | 2523079 A1 | 11/2004 |
| CN | 1711079 A | 12/2005 |
| DE | 19541128 A1 | 4/1997 |
| EP | 0550108 A1 | 7/1993 |
| EP | 0466909 B1 | 6/1995 |
| EP | 0732920 B1 | 10/2003 |
| EP | 1291021 A2 | 12/2003 |
| EP | 1433478 A1 | 6/2004 |
| EP | 1560575 B1 | 9/2006 |

(Continued)

OTHER PUBLICATIONS

The Code of Federal Regulations (Title 21—Food and Drugs, vol. 3, Apr. 1, 2012, § 184.1328 glyceryl behenate.*

(Continued)

*Primary Examiner* — Kortney L Klinkel (74) *Attorney, Agent, or Firm* — Vivicar Law, PLLC (57) ABSTRACT

The invention regards the use of triiodothyronine sulfate, commonly named $T_3S$, as a medicament having thyromimetic activity for the treatment of pathologies due to organic deficiency of triiodothyronine ($T_3$), as such or in association with thyroxine ($T_4$), and pharmaceutical formulations for oral administration thereof.

19 Claims, 3 Drawing Sheets

(56) References Cited

FOREIGN PATENT DOCUMENTS

| | | |
|---|---|---|
| EP | 1322294 B1 | 12/2007 |
| JP | 63-079824 A | 4/1988 |
| JP | 5-255081 A | 10/1993 |
| JP | 7-116031 A | 12/1995 |
| WO | 91/11181 A1 | 8/1991 |
| WO | 95/20953 A1 | 8/1995 |
| WO | 97/17951 A2 | 5/1997 |
| WO | 02/28364 A2 | 4/2002 |
| WO | 03/007994 A2 | 1/2003 |
| WO | 2004/071432 A2 | 8/2004 |
| WO | 2005/004849 A2 | 1/2005 |
| WO | 2008/129303 A2 | 10/2008 |
| WO | 2008/138995 A1 | 11/2008 |

OTHER PUBLICATIONS

AACE Thyroid Guidelines, "American Association of Clinical Endocrinologists Medical Guidelines for Clinical Practice for the Evaluation and Treatment of Hyperthyroidism and Hypothyroidism: AACE Thyroid Task Force", Endocrine Practice, vol. 8, No. 6, Nov.-Dec. 2002, pp. 457-469.

Biondi, Bernadette et al., "Combination Treatment with T4 and T3: Toward Personalized Replacement Therapy in Hypothyroidism?", J Clin. Endocrinol. Metab, Special Feature Clinical Review, 2012, vol. 97, No. 7, doi:10.1210/jc.2011-3399, The Endocrine Society, pp. 1-16.

Chalmers, J.R. et al., "The Synthesis of Thyroxine and Related Substances. Part V. A Synthesis of L-Thyroxine from L-Tyrosine", 1949, pp. 3424-3433, http://pubs.rsc.org|doi:10.1039/JR9490003244.

Chopra, Inder J., "Nature, Sources and Relative Biologic Significance of Circulating Thyroid Hormones", Braverman LE., Utiger RD (eds) The Normal Thyroid, Lippincott, Philadelphia USA, 1991, pp. 126-143.

Chopra, Inder J. et al., "A Radioammunoassay for Measurement of 3,5,3'-Triiodothyronine Sulfate: Studies in Thyroidal and Nonthyroidal Diseases, Pregnancy, and Neonatal Life", Journal of Clinical Endocrinology and Metabolism, 1992, vol. 75, No. 1, pp. 189-194, The Endocrine Society.

De Herder, WW et al., "Rapid and Bacteria-Dependent In Vitro Hydrolysis of Iodothyronine-Conjugates by Intestinal Contents of Humans and Rats", Medical Biology, vol. 64, 1986, pp. 31-35.

Escobar-Morreale, Hector F. et al., "Reivew: Treatment of Hypothyroidism with Combinations of Levothyroxine plus Liothyronine", The Journal of Clinical Endocrinology & Metabolism, 2005, vol. 90, No. 8, pp. 4946-4954, The Endocrine Society, doi: 10.1210/jc.2005-0184.

Faber, J., et al., "Urinary Excretion of Free and Conjugated 3',5'-Diiodothyronine and 3,3'-Diiodothyronine", Journal of Clinical Endocrinology and Metabolism, 1981, vol. 53, No. 3, pp. 587-593, The Endocrine Society.

Goodman & Gilman's "The Pharmacological Basis of Therapeutics", Ninth Edition, Chapter 1 Pharmacokinetics, McGraw-Hill, 1996, p. 5.

Goodman & Gilman's "The Pharmacological Basis of Therapeutics", Ninth Edition, Section XIII Hormones and Hormone Antagonists, McGraw-Hill, 1996, pp. 1394-1395.

Gullo, Damiano et al., "Levothyroxine Monotherapy Cannot Guarantee Euthyroidism in All Athyreotic Patients", PLOS One, 2011, vol. 6, Issue 8, e22552, www.plosone.org, pp. 1-7.

Harrison's Principles of Internal Medicine, 16th edition (Manual), 2005, McGraw-Hill Companies, Inc., p. 2112.

Hemmila, Ilkka et al., "Europium as a Label in Time-Resolved Immunofluorometric Assays", Analytical Biochemistry, 1984, vol. 137, pp. 335-343, Academic Press Inc.

Kung, Mei-Ping et al., "Desulfation of 3,5,3'-Triiodothyronine Sulfate by Microsomes from Human and Rat Tissues", Endocrinology, vol. 122, No. 4, 1988, pp. 1195-1200.

Martindale "The Complete Drug Reference", 36th Edition (Manual), 2009, the Pharmaceutical Press, pp. 2167, 2171-2172, 2174.

Mol, Jan et al., "Synthesis and some properties of sulfate esters and sulfamates of iodothyronines", Endocrinology, vol. 117, No. 1, 1985, The Endocrine Society, pp. 1-7, XP009153115.

Mol, Jan A. et al., "Rapid and Selective Inner Ring Deiodination of Thyroxine Sulfate by Rat Liver Deiodinase", Endocrinology, vol. 117, No. 1, 1986, pp. 8-12.

"Orange Book: Approved Drug Products with Therapeutic Equivalence Evaluations: query on Levothyroxine", FDA U.S. Food & Drug Administration, p. 1-14, Orange Book data updated through May 2012; Patent and Generic Drug Product Data Last Updated Jul. 2, 2012.

"Orange Book: Approved Drug Products with Therapeutic Equivalence Evaluations: query on Liothyronine", FDA U.S. Food & Drug Administration, p. 1-3, Orange Book data updated through May 2012; Patent and Generic Drug Product Data Last Updated Jul. 2, 2012.

Otten, M.H. et al., "Sulfation Preceding Deiodination of Iodothyronines in Rat Hepatocytes", Science, vol. 221, 1983, pp. 81-83.

Roberts, Caroline G.P. et al., "Hypothroidism", Seminar, The Lancet, 2004, vol. 363, pp. 793-803.

Roche, Jean et al., "Hepatic sulphate conjugation of 3,5,3'-triiodo-L-thyronine and the presence of a sulphuric ester of this hormone in bile and plasma", 1959, vol. 33, pp. 461-469.

Rohm and Haas, "Amberlite™ XAD™ 1600N: Macroreticular Polymeric Adsorbent", Mar. 2005, total of 4 pages.

Rooda, Sebo Jan Eelkman et al., "Metabolism of Triiodothyronine in Rat Hepatocytes", Endocrinology, 1989, vol. 125, No. 4, pp. 2187-2197, The Endocrine Society.

Santini, Ferruccio et al., "A Study of Metabolism of Deaminated and Sulfoconjugated Iodothyronines by Rat Placental Iodothyronine 5-Monodeiodinase", Endocrinology, 1992, vol. 131, No. 4, pp. 1689-1694.

Santini, Ferruccio et al., "Metabolism of 3,5,3'-Triiodothyronine Sulfate by Tissues of the Fetal Rat: A Consideration of the Role of Desulfation of 3,5,3'-Triiodothyronine Sulfate as a Source of T3", Pediatric Research, 1992, vol. 31, No. 6, pp. 541-544.

Santini, F. et al., "A Study of the Serum 3,5,3'-Triiodothyronine Sulfate Concentration in Normal and Hypothyroid Fetuses at Various Gestational Stages", Journal of Clinical Endocrinology and Metabolism, 1993, vol. 76, No. 6, pp. 1583-1587.

Santini, Ferruccio et al., "Serum Iodothyronines in the Human Fetus and the Newborn: Evidence for an Important Role of Placenta in Fetal Thyroid Hormone Homeostasis", Journal of Clinical Endocrinology and Metabolism, 1999, vol. 84, No. 2, pp. 493-498.

Santini, Ferruccio et al., "Evidence for the role of the type III-iodothyronine deiodinase in the regulation of 3,5,3'triiodothyronine content in the human central nervous system", European Journal of Endocrinology, 2001, vol. 144, pp. 577-583, ISSN 0804-4643.

Santini, Ferruccio et al., Steady-State Serum T3 Concentrations for 48 Hours Following the Oral Administration of a Single Dose of 3,5,3'-Triiodothyronine Sulfate (T3S), Endocrine Practice, 2014, vol. 20, No. 7, pp. 680-689.

Spaulding, Stephen W. et al., "Studies on the Biological Activity of Triiodothyronine Sulfate", Journal of Clinical Endocrinology and Metabolism, vol. 74, No. 5, 1992, pp. 1062-1067.

The Merck Manual of Diagnosis and Therapy, 17th Edition, (Manual), 1999, pp. 92-95.

Visser, Theo J., "Role of sulfation in thyroid hormone metabolism", Chemico-Biological Interactions, vol. 92, 1994, pp. 293-303, Elsevier Science Ltd.

Wiersinga, Wilmar M., "Thyroid Hormone Replacement Therapy", Hormone Research, 2001, vol. 56(Suppl 1), pp. 74-81.

Office Action—First for Chinese application No. 200380103057.4, mail date Nov. 10, 2006 (English translation).

Office Action—Second for Chinese application No. 200380103057.4, mail date Jun. 22, 2007 (English translation).

Office Action: Rejection Decision for Chinese application No. 200380103057.4, mail date Mar. 28, 2008 (English translation).

(56) References Cited

OTHER PUBLICATIONS

Office Action: Notification of Reexamination for Chinese application No. 200380103057.4, mail date Apr. 8, 2009 (English translation).
Office Action—First for Chinese application No. 200810135762.7, mail date Jun. 10, 2010 (English translation).
Office Action—Second for Chinese application No. 200810135762.7, mail date Oct. 25, 2011 (English translation).
Office Action: Rejection Decision for Chinese application No. 200810135762.7, mail date Aug. 3, 2012 (English translation).
Office Action: Notification of Reexamination for Chinese application No. 200810135762.7, mail date Aug. 1, 2013 (English translation).
Office Action—First for Chinese application No. 201280023319.5, mail date Oct. 20, 2014 (English translation).
Office Action for Japanese application No. 2004-550983, mail date Jan. 19, 2010 (English translation).
Office Action: Decision Refusal for Japanese application No. 2004-550983, mail date Aug. 24, 2010 (English translation).
Office Action: PreTrial Re-Examination for Japanese application No. 2004-550983, mail date Jan. 31, 2012 (English translation).
Office Action: Trial Decision for Japanese application No. 2004-550983, mail date May 21, 2013 (English translation).
Office Action for Japanese application No. 2010-288189, mail date Jan. 8, 2013 (English version).
Office Action: Notice of Allowance for U.S. Appl. No. 13/755,279, mail date Jan. 30, 2015.
Office Action: Reexamination Decision for Chinese application No. 200810135762.7, mail date Jan. 26, 2015 (English translation).
Office Action—First: for Japanese application No. 2014-503150, mail date Feb. 24, 2015 (English translation).
Office Action for Chinese application No. 200810135762.7, mail date Jun. 8, 2015 (English translation).
Office Action for Chinese application No. 201280023319.5, mail date Sep. 9, 2015 (English translation).
Office Action: Final for U.S. Appl. No. 13/755,279, mail date Jul. 31, 2014.
Office Action: Notice of Allowance for U.S. Appl. No. 13/755,279, mail date Apr. 9, 2015.
Application, National Phase of PCT/EP2012/056274 (WO2012/1367671A1), U.S. Appl. No. 14/110,237, filed Oct. 7, 2013, with Preliminary Amendment.
U.S. Appl. No. 14/249,542, Continuation of U.S. Appl. No. 14/110,237, filed Apr. 10, 2014, with Preliminary Amendment, filing date, Apr. 14, 2014.
Feigenbaum, J. et al., "Simplified Method for the Preparation of Aromatic Sulfuric Acid Esters", Journal of the American Chemical Society, American Chemical Society, Washington DC, vol. 63, 1941, pp. 3259-3530, XP-002522192, ISSN: 0002-7863.
Mol, Jan et al., "Synthesis and some properties of sulfate esters and sulfamates of iodothyronines", Endocrinology, vol. 117, No. 1, 1986, The Endocrine Society, pp. 1-7, XP009153115.
Office Action for U.S. Appl. No. 10/532,447, mail date May 14, 2014, total: 28 pp.
PCT International Search Report and Written Opinion for PCT/EP2012/056274, mail date Jun. 14, 2012.
PCT International Search Report and Written Opinion for PCT/EP2012/056274, mail date Aug. 8, 2012.
PCT Written Opinion of the International Preliminary Examining Authority for PCT/EP2012/056274, mail date Mar. 12, 2013.
PCT Written Opinion of the International Preliminary Examining Authority for PCT/EP2012/056274, mail date May 31, 2013.
PCT International Preliminary Report on Patentability for PCT/EP2012/056274, mail date Aug. 27, 2013.
Office Action for U.S. Appl. No. 13/755,279, mail date Dec. 4, 2013.
Bunevicius R. et al., "Effects of Thyroxine as Compared with Thyroxine plus Triiodothyronine in Patients with Hypothyroidism", The New England Journal of Medicine, vol. 340(6), pp. 424-429, Feb. 11, 1999.
Chopra I. J. et al, "Demonstration of thyromimetic effects of 3,5,3'-triiodothyronine sulfate (T3S) in euthyroid rats" Thyroid 1996 United States, vol. 6, No. 3, 1996, pp. 229-232, XP009027310.
Herfindal, E. et al., Clinical Pharmacy and Therapeutics: Fifth Edition, Williams & Wilkins, 1992.
LoPresti Jonathan S. et al: "Characteristics of 3,5,3'-Triiodothyronine Sulfate Metabolism in Euthyroid Man" Journal of Clinical Endocrinology and Metabolism, vol. 73(4), pp. 708-709, 1992.
Mol J. et al., "Synthesis and some properties of sulfate esters and sulfamates of iodothyronines", Endocrinology, vol. 117(1), pp. 1-7, Jul. 1985, NCBI Pub Med, www.pubmed.gov.
PCT Search Report for PCT/EP03/12584, mail date Mar. 25, 2004.
PCT International Preliminary Examination Report for PCT/EP03/12584, mail date Feb. 24, 2005.
Rudnic, E. et al., "Oral Solid Dosage Forms", Remington: The Science and Practice of Pharmacy, Ch. 92, 19th ed., pp. 1615-1649, Mack Publishing Company, Easton, PA 18042, 1995.
Santini Ferruccio et al: "Thyromimetic effects of 3,5,3'-triiodothyronine sulfate in hypothyroid rats" Endocrinology, vol. 133, No. 1, 1993, pp. 105-110, XP002272821.
Wu, S-Y et al., "Thyroxine Sulfate is a Major Thyroid Hormone Metabolite and a Potential Intermediate in the Monodeiodination Pathways in Fetal Sheet", vol. 131(4), Endocrinology, pp. 1751-1756, 1992.
The Code of Federal Regulations (Title 21—Food and Drugs, vol. 3, Apr. 1, 2012, §184.1328 glyceryl behenate).
Office Action for Australian application No. 2012238665, mail date Feb. 22, 2016.
Office Action for Chinese application No. 201280023319.5, mail date May 26, 2016.
Office Action for European application No. 12712124.2, mail date Dec. 8, 2015.
Office Action for Israel application No. 228757, mail date Oct. 14, 2015 (English translation).
Office Action for Russian application No. 2013149419, mail date Jan. 11, 2016 (English translation).
Office Action for Russian application No. 2013149419, mail date Apr. 18, 2016 (English translation).
Office Action for Chinese application No. 200810135762.7, mail date Aug. 19, 2016 (English translation) [B0496].

* cited by examiner

Figure 1 Panel a)

Figure 1 Panel b)

Figure 4

3,5,3'-TRIIODOTHYRONINE SULFATE AS THYROMIMETIC AGENT AND PHARMACEUTICAL FORMULATIONS THEREOF

CROSS-REFERENCE TO RELATED APPLICATIONS

This application is a continuation application of, and claims priority to co-pending U.S. application Ser. No. 13/083,047, filed Apr. 8, 2011, which is hereby incorporated by reference in its entirety.

FIELD OF THE INVENTION

The present invention regards the use of 3,5,3'-triiodothyronine sulfate, usually named triiodothyronine sulfate or $T_3$ sulfate ($T_3S$), as an active principle, alone or in combination with thyroxine, in the treatment of pathologies due to organic deficiency of 3,5,3'-triiodothyronine. Accordingly, the same is usable for the preparation of thyromimetic pharmaceutical compositions.

BACKGROUND OF THE INVENTION

A number of iodothyronines are present in blood, which are directly produced by thyroid gland or are the result of peripheral metabolism of other iodothyronines. Among them, 3,5,3'-triiodothyronine (acronym $T_3$) is deemed to be the biological active form of thyroid hormone (TH), because it has shown high affinity for the specific receptors of the same and is normally present in serum at a concentration sufficient for the activation of said receptors.

The main secretion product of thyroid gland in the healthy adult is thyroxine, commonly designated with the acronym $T_4$. It is peripherically converted to its biologically active form, $T_3$ (Ref. 1), through enzymatic removal of an iodine atom from the external aromatic ring of the molecule by both type I and type II 5'-iodothyronine monodeiodinases (type I MD and type II MD, respectively). This metabolic pathway is the main mechanism of endogenous production of $T_3$; thus, $T_4$ can properly be considered a pro-hormone. On the other hand, a minor part of $T_3$ is also directly secreted by thyroid. On average, the amount of $T_4$ produced in an adult being of 70 Kg weight every day amounts to 100 μg, while the total production of $T_3$ amounts to around 25 μg. 4-8 μg of $T_3$ out of said 25 μg are directly secreted by thyroid and the remaining ones derive from the peripheral conversion of $T_4$.

$T_3$ undergoes two different metabolic pathways. The main metabolic pathway consists in the partial deiodination of the inner aromatic ring by type III 5-iodothyronine monodeiodinase (type III MD) to give 3,3-diiodothyronine, which is biologically non-active and is further metabolized through deiodination or sulfoconjugation. The other metabolic pathway regards around 20% of the total amount of $T_3$ produced by the body and brings on sulfoconjugation of $T_3$ to give $T_3S$, which is not able to bond to the thyroid hormones (Ref. 2), thus resulting biologically non-active (Ref. 3).

Contrary to what happens with $T_3$, $T_3S$ is not deiodinated by type III MD. Rather, it is an excellent substrate for type I MD (Ref. 4), which converts it very quickly into to 3,3'-diiodothyronine sulphate. Thus it has been widespread common knowledge that, in the healthy adult being, sulfoconjugation of $T_3$ to give $T_3S$ represents a way for speeding up the catabolism of $T_3$, so facilitating its biliary and urinary excretion. Actually, it was found that serum levels of $T_3S$, physiologically low in the healthy adult, are higher when type I MD activity is reduced.

Yet, it was found that, just in some body districts and organs, sulfatases exist which, under particular physiological conditions and situations, are able to convert again $T_3S$ into its active form $T_3$ (Ref's. 7-9).

Such enzymes have been described in the intestinal microflora as well as in body tissues like liver, kidneys and nervous central system (Ref. 10).

Recently, it has been found that endogenous $T_3S$ levels in serum are quite high during intrauterine life and as such are kept by the body, i.e. higher than the ones normally found in the adult being, at least until the forth month of postnatal life (Ref. 11). Considering the essential role played by thyroid hormones during growth, in particular as far as nervous central system functions are involved, hypotheses have been made about the possibility that, in this tissue, $T_3S$ may also possibly be used by the body as an occasional source of $T_3$, if and when needed, during the first period of life. Studies performed on autoptic specimens of human nervous cerebral tissue post-mortem showed that the amount of $T_3$ in the same results limited by type III MD (Ref. 12). While this enzyme does not attack $T_3S$, it has been surmised that $T_3S$ may exceptionally represent an alternative endogenous source of $T_3$ hormone in those tissues which contain sulfatases able to reconvert $T_3S$ into its active form, just in case a particular need of the hormone arises in said tissues (Ref's. 8, 13).

Further studies have been performed, aimed at ascertaining the effective role played by $T_3S$ during production and metabolism of thyroid hormones. Said studies have recently demonstrated that when administered by intraperitoneal (i.p) administration in single or 3 to 10 daily doses a thyromimetic effect is observed in hypothyroid rats (Ref. 10). In euthyroid rats (Ref. 14) T3S, administered i.p., shows a thyromimetic effect on several parameters such as body weight and TSH serum levels. In both references $T_3S$ has shown a potency of around one fifth that of $T_3$. Moreover both treatments with $T_3S$ and with $T_3$ produced a significant reduction of serum levels of thyreotropic hormone (TSH) in euthyroid rats, thus showing to possess similar capability in inhibiting its secretion. On the contrary, in the case of hypothyroid rats, $T_3S$ showed a poor capability of inhibiting TSH secretion when compared to $T_3$. It is well known that TSH is a highly responsive indicator to the functional status of thyroid gland and detects the smallest alterations of its hormonal secretion. Actually, its levels are higher under conditions of reduced thyroid functionality, even in those conditions that are defined as sub-clinical, while they are reduced when an excess of thyroid hormones are present. As a consequence, $T_3S$ activity seems non-comparable to $T_3$ as far as its capability of inhibition on formation of TSH is involved.

Therefore, particularly in view of the latest studies the biological role of $T_3S$ is still controversial.

In fact, its main, well-grounded and universally accepted, feature is its non-biological activity, i.e. it is a biologically inert metabolite of $T_3$ (Ref's. 2 and 3), and the sulfation pathway is regarded as a metabolic activator of $T_3$ catabolism (Ref. 5).

On the other hand, only in particular tissues and under exceptional critical conditions due to shortage of thyroid hormone in those tissues, it has been shown its potential as an endogenous local source of $T_3$.

As a result, today the skilled technician is still facing a complex, somewhat conflicting, situation, which highlits only some of the biological characteristics of the product and needs more exhaustive in depth studies.

To the best of our knowledge, however, none of the several documents forming the state-of-the-art discloses, shows or suggests the possibility of using this metabolite of $T_3$ in therapy. No close prior-art document, either of experimental nature or substantially speculative, either taken alone or in combination with other related documents, suggests the use, or even the potential use of $T_3S$ as a medicament, taken as such or preferably in combination with other thyroid hormones or pro-hormones, like, for example $T_4$. The fact that, only in some specific tissues of the body and under particular, peculiar circumstances, part of $T_3S$ can be reconverted into $T_3$ does not mean, nor implies, nor suggests that it is possible to generalize this feature to the whole organism through exogenous administration of the product. In particular, there is no suggestion that oral administration of the product, even in protected form according to known methods of the pharmaceutical technique, may render it bioavailable also because it is well known that in those districts where suitable sulfatases are not present the same is rapidly metabolized and excreted through the bile and urines.

SUMMARY OF THE INVENTION

It has now unexpectedly been found, and this is one of the aspects of the present invention, that $T_3S$ (triiodothyronine or 3,5-diiodo-O-[3-iodo-4-(sulphoxy)phenyl]-L-thyronine), as the only active principle in a suitable composition or in association with other thyroid hormones or pro-hormones, preferably $T_4$ (Tyroxine, or 3,5,3',5'-tetraiodothyronine) and properly formulated according to the desired application for oral administration is particularly useful as a medicament to be used in all those pathologies caused by insufficient production by the body of the needed quantities of active thyroid hormones, in particular $T_3$.

Another aspect of the present invention is a non-radioactive immunoassay for $T_3S$ quantitation, preferably based on chemiluminescence and the reagents developed therein.

A further object of the present invention is a method for the therapeutic treatment of a hypothyroid condition, which comprises the oral administration of $T_3S$ or the combination $T_3S$ and $T_4$ as a thyroid hormone replacement therapy to a subject in need thereof.

According to a preferred embodiment oral administration is accomplished by solid compositions, preferably in the tablet form, comprising $T_3S$ alone or in combination with a second active principle, tyroxine ($T_4$), in a dose comprised for $T_3S$ of from 1 to 1000 μg, preferably 2.5-500 μg and $T_4$ of from 1 to 800 μg.

Preferred active principle quantities in the formulation comprising two active principles, are the following: $T_3S$ 5-250 μg and $T_4$ 5-400 μg, $T_3S$ 10-100 μg and $T_4$ 10-200 μg.

In any case, the preferred ratio between active principles ($T_4$:$T_3S$) is comprised to from 10:1 to 0.1:1, with a more preferred range comprised from 5:1 to 1:1. Even more preferred is the range comprised from 3:1 to 2:1 ($T_4$:$T_3S$).

Said compositions include diluents, glidants or lubricants and disintegrants and in a preferred embodiment consist essentially of: calcium carbonate, glycerol dibehenate, croscarmellose sodium salt, hydrate colloidal silica, magnesium stearate and microcrystalline cellulose, in an even more preferred embodiment these components are present in the amounts described below for a 80-150 mg tablet:

| | |
|---|---|
| Calcium carbonate | 20-40 mg, preferably 25-35 mg, more preferably 30 mg |
| Glycerol dibehenate | 2-15 mg, preferably 4-8 mg, more preferably 5 mg |
| Croscarmellose sodium salt | 1-10 mg, preferably 2-6 mg, more preferably 3.5 mg |
| Hydrate colloidal silica | 0.1-5 mg, preferably 0.5-4, more preferably 2 mg |
| Magnesium stearate | 0.01-2 mg, preferably 0.1-1 mg, more preferably 0.5 mg |
| Microcrystalline cellulose | Up to 110 mg |

This composition is endowed with optimal dissolution rates and stability of the active principle(s) for at least 24 months.

DETAILED DESCRIPTION OF THE INVENTION

It has been now been surprisingly found that $T_3S$ or salts thereof is not only a physiologic $T_3$ catabolite, but that it may be also provided as a drug and administered in hypothyroid conditions. Accordingly, this represents the main aspect of the invention.

Furthermore, it has been found that $T_3S$, once administered is converted to $T_3$ and allows maintenance of steady levels of $T_3$ in the body for long times (from 12 to at least 18 hrs, more preferably at least 48 hrs). This is not only particularly useful when a supplement thyroid hormone in its most active form is needed, but, once more, is completely unexpected given the rapid metabolism synthetic $T_3$ undergoes once administered. In this case in fact a peak level is detected in serum at about 2-3 hours and after that rapidly and completely cleared from blood within 12-24 hrs.

Furthermore, it has also been found that $T_3S$ can be administered orally and this represents a further and particularly advantageous aspect of the invention. In fact its biological activity, measured for example by total $T_3$ levels in the serum of thyrectomized individuals, is detected after oral administration. This result is quite unexpected because, at variance with thyroid hormones which are not very soluble in water, $T_3S$ or salts thereof is a polar molecule whose gastrointestinal absorption was expected to be rather inefficient. Therefore the present invention discloses that oral administration is possible and that by this route: a) $T_3S$ is found in the bloodstream thus demonstrating that it crosses the gastrointestinal barrier, b) is converted into the more active thyroid hormone, $T_3$, c) maintains $T_3$ levels in serum after administration for quite a long time (at least 48 hours).

According to this finding, a further object of the present invention is represented by a method for the therapeutic treatment of a hypothyroid condition, which comprises the oral administration of $T_3S$ or the combination $T_3S$ and $T_4$ as a thyroid hormone replacement therapy for a subject in need thereof. Clinical signs of hypothyroidism are the following: asthenia, fatigue, skin dryness, somnolence, speech fluency impairment, cold intolerance, weight gain and/or memory deficit. Accordingly, any of these conditions may be improved by the oral administration of $T_3S$ alone or in combination with $T_4$.

In general, oral administration of $T_3S$ and salts thereof in pharmaceutical compositions is proposed according to a preferred aspect of the invention for treating any hypothyiroid conditions or for any $T_3$ replacement therapy. The therapeutic treatment comprises administering compositions comprising $T_3S$, either alone in a dose comprised for $T_3S$ of from 1 to 1000 µg, preferably from 2.5 to 500 µg, more preferably from 5 to 250 µg, or in combination with a second active principle, thyroxine ($T_4$) (combination compositions) wherein $T_4$ is present from 1 to 800 µg.

Preferred active principle quantities in the combination compositions are the following: $T_3S$ 5-250 µg and $T_4$ 5-400 µg, $T_3S$ 10-100 µg and $T_4$ 10-200 µg.

In any case, for combination compositions a preferred ratio between active principles ($T_4$:$T_3S$) is comprised from 10:1 to 0.1:1, with a more preferred range comprised from 5:1 to 1:1. Even more preferred is the range comprised from 3:1 to 2:1 ($T_4$:$T_3S$).

Preferred administration of the compositions is in a single daily dosage form.

Particularly preferred in the therapy of hypothyroidism, representing a further aspect of the present invention, is the association of $T_3S$ with $T_4$. The hormonal association which, in theory, should more accurately mime the normal thyroid secretion is represented by a combination of $T_4$ with $T_3$. Actually, pharmaceutical compositions comprising both of said iodothyronines, formulated in proportions similar to the ones of the normal physiologic secretion, have already been tried and marketed. Unfortunately, the oral simultaneous administration of $T_4$ with $T_3$ was not able to reproduce the normal thyroid hormones serum levels, because of pharmacokinetics of $T_3$. In fact, $T_3$ undergoes a very quick absorption and an equally quick elimination after oral administration; its elimination rate is about 20 times higher than the one of $T_4$. For this reason administration of $T_3$ gives raise to a dangerous peak excess in hormone concentration, if compared to the normal physiologic levels, followed by a much too fast drop to sub-physiologic levels. Thus, today most of the specialised physicians prefer using $T_4$ alone, even if in this way production of $T_3$ only depends on the periferic deiodination of $T_4$, because direct secretion of $T_3$ by thyroid does not exists or is seriously insufficient.

On the contrary, the association of the invention avoids the above problems, because it has unexpectedly been found that, for example, after oral administration, $T_3S$ provides $T_3$ serum levels that increase in a gradual way and keep steady for long periods of time, thus preventing the formation of too high peaks.

Another unexpected advantage deriving from the use of $T_3S$ in the treatment of pathologies due to organic deficiency of $T_3$ consists in its recently found systemic thyromimetic activity linked to a poor inhibition of TSH secretion. This effect is particularly useful in the case of thyroidectomized patients suffering from thyroid carcinoma, when administration of $T_4$ must be suspended in view of carrying out radiotherapy. In such a case administration of $T_3S$ instead of $T_4$ may alleviate a patient's symptoms or disease, such as asthenia, fatigue, skin dryness, somnolence, speech fluency impairment, cold intolerance, weight gain and/or memory deficit without interfering with radioactive iodine (usually $^{131}I$) radiotherapy.

According to this observation, a further aspect of the invention relates to $T_3S$ administration in thyroidectomized patients in case of $^{131}I$ radiotherapy when $T_4$ administration must be suspended. In fact, T4 is usually suspended at least 40 days before radiotherapy to allow an optimal radioisotope uptake. The lack of thyroid hormones for such a long time is usually very badly tolerated by the organism which is completely depleted of thyroid hormones within a few days, thus suffering from asthenia, fatigue, skin dryness, somnolence, speech fluency impairment, cold intolerance, weight gain or memory deficit. In contrast, $T_3S$, due to its low thyromimetic properties, can be administered, preferably by the oral route, up to at least 5 days, more preferably up to at least 4, 3, or 2 days, before radiotherapy.

Another further advantage of $T_3S$ in the therapy of hypothyroidism regards its autolimitation capability. In fact, it is actively deiodinated by type I MD, which, on its part, is stimulated by thyroid hormones. In hypothyroid subjects type I MD activity is reduced; thus $T_3S$ elimination is slowed. As a matter of fact, its effect on the body is greater. On the contrary, in case of over administration, type I MD activity is increased, thus giving more $T_3S$ elimination, i.e. limiting possible undesired collateral effects.

Last but not least, a further advantage of $T_3S$ is represented by the fact that it is a metabolite normally present in the body, usually non-active, i.e. non-toxic.

Accordingly, another main aspect of the present invention regards pharmaceutical formulations comprising $T_3S$ as an active principle, as such or in combination with other thyroid hormones or pro-hormones. Particularly preferred are formulations comprising $T_3S$ in association with $T_4$.

The preferred ratio of the two active principles ($T_4$:$T_3S$) in composition scomprising both active principles ranges from 10:1 to 0.1:1, with a more preferred range comprised from 5:1 to 1:1. Even more preferred is the range comprised from 3:1 to 2:1 ($T_4$:$T_3S$).

Said formulations differ in the dosage of the active principle or principles, or in the type of pharmaceutical form provided, depending on the administration route used with enteral administration being preferred.

According to this embodiment, compositions for oral administration, either liquid or solid are both suitable. Preferred liquid compositions should take into account the generally poor solubility of thyroid hormones such as $T_4$ and salts thereof, as well as the usually good solubility of $T_3$ sulphate and salts thereof. Furthermore, the use of lactose, glucose and sucrose should be avoided.

The preparation of specific pharmaceutical formulations in response to particular needs will be described in the following.

Solid Compositions.

It is known that thyroid hormones and especially levothyroxine sodium are compatible with some excipients but incompatible with others. Carbohydrates, such as starch and maltodextrin, are compatible with thyroid hormones, whereas lactose, glucose and sucrose, have been determined to be incompatible. By the use of suitable compatible diluents, glidants or lubricants and disintegrants, thyroid hormones can be formulated into tablets, capsules, or powder dosage forms.

Thus, preferred compositions of the present invention are prepared in the substantial absence of lactose, glucose, sucrose, polyvinylpyrrolidone, and/or a Poloxamer. According to this embodiment, the solid composition comprises diluents or fillers, glidants and/or lubricants and disintegrants. The compositions may also further comprise excipients, stabilizers, preservatives or dissolution enhancers.

Preferred diluents are cellulose derivatives, such as microcrystalline cellulose, powdered cellulose, silicified microcrystalline cellulose, cellulose acetate, ethyl- or methylcellulose or salts thereof. However, other diluents may be used, such as kaolin, starch and derivatives thereof, or sodium or other alkaline inorganic salts such as trisodium phosphate, tricalcium phosphate, calcium carbonate or magnesium carbonate.

Suitable disintegrants for use in the present invention include corn starch, croscarmellose and salts thereof (i.e. croscarmellose sodium) and crospovidone or salts thereof. However other disintegrants may be used such as, polymethacrylates and maltodextrin or salts thereof, pregelatinized starch and sodium starch glycolate or sodium alginate, sometimes referred to as diluents as well.

Suitable lubricants for use in the present invention comprise silicates in general, including colloidal silicon dioxide hydrate silicon dioxide, hydrate colloidal silica, talc, as well as magnesium or zinc stearate the preferred ones.

Suitable glidants or lubricants are chosen among glycerol dibehenate, tribasic calcium phosphate, starch derivatives, talc, magnesium and zinc stearate, sodium stearate fumarate and sodium and magnesium lauryl sulphate. Prefererd glidants or lubricants are glycerol dibehenate or tribasic calcium phosphate.

The term glidant comprises agents working also as lubricants, and for those, such as talc, magnesium or zinc stearate or sodium dibehenate, accordingly, classification might be interchangeable.

Flavorants and colorants may be added if desired as additional optional ingredients.

Thyroid hormones, especially levothyroxine sodium and $T_3S$ are particularly stable in connection with cellulose derivatives. According to this embodiment solid dosage compositions with improved and superior, stability, content uniformity, good tableting and dissolution properties which comprise $T_3S$ or salts thereof alone or in combination with $T_4$ or salts thereof in the quantities above disclosed further in combination with a cellulose derivative, wherein microcrystalline cellulose or silicified microcrystalline cellulose are particularly preferred.

Thyroid hormones are preferably prepared by the synthetic route (e.g. as described for $T_3S$ in Mol and Visser, Endocrinology 1985, 117 N.1, 1:1-8).

In the solid composition, diluents are preferably present in a predominant amount, preferably in the range of 50 to 99.99% by weight. More preferably they are present in an amount of from 60 to 80% by weight, more preferably from 65-75% by weight.

According to a preferred embodiment, cellulose or derivatives thereof are present and preferably a second diluent is also present, preferably calcium carbonate, up to 35% of the total diluent w/w.

Preferred glidants, are selected from the group consisting of glycerol dibehnate (most preferred), talc and silica derivatives, among which magnesium trisilicate, starch or derivatives thereof, amides, tribasic calcium phosphate, are usually present in the composition in a quantity range from 1 to 10%, most preferably 4 to 6% (w/w).

Lubricants are preferably selected in the group consisting of: magnesium or zinc stearate, hydrate colloidal silica and talc, more preferably magnesium stearate and hydrate colloidal silica, in a total quantity of from 0.1 to 7% even more preferably the first one comprised from 0.1 to 2% and the second comprised from 0.5 to 5%.

Disintegrants for use in the present invention include starch, croscarmellose sodium and crospovidone. Preferred is croscarmellose or sodium salts thereof in a quantity ranging from 0.5 to 10% even more preferably comprised from 1-5%, most preferably comprised from 2- to 4%.

The moisture content of the solid dosage form, such as of a capsule or tablet, is also important. It is preferred that the moisture content is not higher than 15%, even more preferably not higher than 10%. A buffer system may be present as a stabilizer in the solid dosage form.

A significant advantage of the preparations of the present invention is that they can be prepared as a direct compression formula, dry granulation formula, or as a wet granulation formula, with or without preblending of the drug, although preferably with preblending, and still achieve remarkable stability of the resulting solid dosage form preparation.

The amount of the thyroid hormone in the preparations of the present invention can vary widely, mainly depending on the administration protocol. However, due to the high potency exhibited by most of the thyroid hormones, and especially levothyroxine sodium, normally very low amounts of this thyroid hormone will be utilized.

The solid compositions comprising $T_3S$ alone comprise $T_3S$ of from 1 to 1000 µg; according to a further embodiment they comprises also $T_4$ (tyroxine): according to this embodiment (combination compositions) $T_3S$ is present in a quantity of from 2.5-500 µg and $T_4$ of from 1 to 800 µg.

Even more preferred active principle quantities in the formulation comprising two active principles are the following: $T_3S$ 5-250 µg and $T_4$ 5-400 µg, $T_3S$ 10-100 µg and $T_4$ 10-200 µg.

In any case, the preferred ratio between active principles ($T_4$:$T_3S$) is comprised from 10:1 to 0.1:1, with a more preferred range comprised from 5:1 to 1:1. Even more preferred is the range comprised from 3:1 to 2:1 ($T_4$:$T_3S$).

In the present specification, solid composition percent values refers to weight/weight (w/w) ratios and the pharmaceutical dosage form is of about 50-200 mg.

The compositions of the present invention are usually prepared by blending the thyroid hormones with microcrystalline cellulose, calcium carbonate, glycerol dibehenate, crosscarmellose salt, hydrate colloidal silica.

The resulting blend can be lubricated with magnesium stearate and tableted using a tablet press.

According to the invention, the solid composition of the invention are prepared in tablets and comprise either $T_3S$ as the only active principle or $T_3S$ in combination with a second active principle, preferably $T_4$, in the quantities and ratios above indicated, together with the following diluents, disintegrants, glidants, lubricants or excipients. In a preferred embodiment, the composition contains 1 to 1000 µg $T_3S$, in a more preferred embodiment the compositions include 2.5 to 500 µg $T_3S$ or more preferably 5-250 µg $T_3S$ and the following further ingredients (in amounts described below for a 80-150 mg tablet):

|  | Amount per Tablet |
| --- | --- |
| Calcium carbonate | 20-40 mg, preferably 25-35 mg, more preferably 30 mg |
| Glycerol dibehenate | 2-15 mg, preferably 4-8 mg, more preferably 5 mg |
| Croscarmellose sodium salt | 1-10 mg, preferably 2-6 mg, more preferably 3.5 mg |
| Hydrate colloidal silica | 0.1-5 mg, preferably 0.5-4, more preferably 2 mg |
| Magnesium stearate | 0.01-2 mg, preferably 0.1-1 mg, more preferably 0.5 mg |
| Microcrystalline cellulose | Up to 110 mg |

For combination compositions $T_3S$ is preferably present in a quantity of from 2.5-500 µg and $T_4$ of from 1 to 800 µg, or, even more preferably: T₃S: 5-250 µg and T₄: 5-400 µg, or T₃S: 10-100 µg and T₄ 10-200 µg.

It is intended that the above quantities preferably refer to about 110 mg tablets, preferably for daily single dosage administration, even though the skilled artisan may envisage adjustments due to alternative composition forms and/or therapeutic treatment protocols. Due to the conversion rates of T₃S to T₃ within the body a single administration every two or three days may be also envisaged.

According to the embodiment above for tablets, the following composition for T₃S or T₄ and T₃S as active principle(s) (0.01-1% w/w) represents a further object of the present invention:
- a diluent selected from cellulose or derivatives thereof, preferably together with a second diluent, preferably calcium carbonate, up to 35% of the total diluent (w/w);
- a glidant, selected from glycerol dibehnate (most preferred), talc, silica derivatives among which magnesium trisilicate, amides, tribasic calcium phosphate, are usually present in the composition in a quantity range from 1 to 10%, most preferably 4 to 6% (w/w);
- a disintegrant selected from starch, croscarmellose sodium and crospovidone. Preferred is croscarmellose sodium salt in a quantity ranging from 0.5 to 10% even more preferably comprised from 1-5%, most preferably comprised from 2- to 4% (w/w);
- a lubricant selected from magnesium stearate, hydrate colloidal silica and talc, more preferably magnesium stearate and colloidal silica, in a total quantity range comprised from 0.1 to 7% even more preferably the first one comprised from 0.1 to 2% and the second comprised from 0.5 to 5% (w/w).

Different tablet weight and active principle contents or different administration protocols may be envisaged for those skilled in the art.

The tablets according to the preferred embodiment show optimal dissolution rates (see table below) and an optimal stability of the active principle(s) (at least 24 months).

The following properties measured in conditions according to ICH Guidelines:

| | |
|---|---|
| Dissolution test | ≥75% after 45' |
| Moisture content | ≤10% |
| Resistance to crushing | ≥20 N |
| HPLC Title T3S | 90-110% |
| HPLC Title T4 | 90-110% |

Liquid compositions, for example obtainable by crushing one or more tablets and dissolving such a mixture or the blended mixture in aqueous solutions are also possible. Optionally, trace amount (i.e. below 5%) of a pharmaceutically acceptable antioxidant is also present. It is contemplated that such compounds may include, for example, ammonium chloride and/or one or more iodide donors (e.g., sodium iodide).

The compositions of this invention may further comprise one or more physiologically acceptable formulation excipients, such as those described in "Remington, J. P, Gennaro, A. R., Remington's Pharmaceutical Sciences, Mack Publishers, Easton, (20th Edition, 2000).

The compositions of this invention are particularly suitable for oral administration.

The term "oral formulation" means that the active ingredient(s) is formulated into a product suitable for administering to an animal via the mouth. These formulations may include apart from the solid compositions described above, for example, liquids or semi-liquids, gels, pastes, oral sprays, buccal formulations, or animal feeds containing the active ingredients. Said liquid or semi-liquid compositions are typically aqueous solution.

The pharmaceutical compositions described above are prepared preferably as tablets, obtainable by direct compression of the mixture above described in powder. In some such embodiments, for example, the process further comprises combining T₃S or T₃S and T₄ in the solid compositions described above with an aqueous composition optionally comprising a buffer for the preparation of a pharmaceutical liquid composition for oral administration.

It should be kept in mind that when the association is taken into account, the formulations of the present invention will also possibly comprise individually formulated doses of T₃S and T₄, for sequential or combined administration. In this case, one suitable kit is provided, which permits administration of said active principles in ways that can differ from patient to patient, depending on the needed therapeutic application. In such a way, the specialized physician will have a wide choice of changing the prescription according to the actual need of the patient.

Just by way of a non-limitative example, in the case of oral administration, one package containing two individual blisters, which have different shape and/or color and/or different contents and/or doses, may suit the desired scope. Other possibilities exist and are easily available to the expert of the field.

The pharmaceutical compositions of the present invention are usable in the treatment of pathologies due to organic deficiency of triiodothyronine (T₃), like, for example, original hypothyroidism from autoimmune thyroid affections, hormonal production defects, thyroidectomy, congenital hypothyroidism, as well as some disorders due to reduced activity of type I 5'-iodothyronine monodeiodinase (type I MD) which is induced, for example, by hypothyroidism, non thyroidal systemic illnesses, fast, selenium shortage and so on.

Once administered to a human patient in need thereof, preferably suffering from a hypothyroid conditions, T₃S levels can be measured and adjusted accordingly by a non-radioactive method immunoassay, either based on colorimetric, fluorescent or chemiluminescent detection.

Accordingly, a further embodiment of the invention is represented by a non radioactive immunoassay. Preferably the immunoassay is an Enzyme Linked Immuno Assay (ELISA), more preferably a competitive ELISA in which increasing amounts of T₃S compete for the binding to a solid phase bound anti-T₃S antibody, (e.g. the polyclonal disclosed in Chopra et al., J. Clin. Endocrinol. Metab., 1992, 75: 189-194) with a fixed amount of T₃S conjugated with an avidin-derivative detectable moiety (i.e. biotin), preferably carried out in a multi-well plate. More preferably, the avidin-derivative is a streptavidin and the detectable moiety comprises a chemiluminescent moiety (such as Alkaline Phosphatase or Horseradish Peroxidase), preferably HRP. The use of biotin-avidin interaction, combined with the various detection luminescence as techniques for signal development, allows signal amplification and increased sensitivity, comparable to a RIA test (see i.e. Chopra et al., J. Clin. Endocrinol. Metab., 1992, 75: 189-194) but without the need for radioactivity—a clear advantage over the prior art. The ELISA assay, the T₃S-biotin reagent and its synthesis, and kits for T₃S quantitation comprising such reagent, represent a further object of the present invention.

As an alternative embodiment, the T₃S immunoassay is developed for a particular fluorescence technique, known as DELFIA® (Dissociation Enhanced Lanthanide Fluorescence ImmunoAssay) by which the required sensitivity is obtained. This assay, the synthesized reagents, and kits for $T_3S$ quantitation comprising said reagents represent a further object of the invention.

Thus, accordingly, a DTPA-$T_3S$ monoamide (3,5-Diiodo-N-[[(carboxymethyl) [2-[(carboxymethyl) [2-[bis(carboxymethyl) amino]ethyl]amino]ethyl]amino]acetyl]-O-[3-iodo-4-(sulfooxy)phenyl]-L-tyrosine) of Formula I, represents a chelating compound according to a preferred embodiment:

Formula I

Other molecules can be designed and synthesized by an expert in the field, through conjugation of $T_3S$ with a variety of chelating moieties, among those suitable for complexation of lanthanide ions, e.g., nitrilotriacetic acid (NTA), ethylenediaminetetraacetic acid (EDTA), ethylenediamine-N,N'-bis(2-hydroxyphenylacetic acid) (EDDHA), ethylenediaminedisuccinic acid (EDDS), propanediaminetetraacetic acid (PDTA), diethylenetriaminetetraacetic acid (DTTA), diethylenetriaminepentaacetic acid (DTPA), and similar molecules. Conjugation between the chelating agent and $T_3S$ can be obtained by a variety of methods already known to the expert in the field, including a direct amide bond formation, as exemplified in Experimental Part, or the use of bifunctional chelating agents, that may even be commercial products, such as (S)-1-p-isothiocyanatobenzyldiethylenetriaminepentaacetic acid (DTPA isothiocyanate—Invitrogen cat. I24221), or similar products.

Suitable lanthanide metals to be used as chelate labels are selected in the group consisting of: samarium, terbium, dysprosium and europium.

Particularly preferred is the Europium chelate 3,5-Diiodo-N-[[(carboxymethyl)[2-[(carboxymethyl)[2-[bis(carboxymethyl)amino]ethyl]amino]ethyl]amino]acetyl]-O-[3-iodo-4-(sulfooxy)phenyl]-L-tyrosine (Formula II).

washed with water and dissolved in an water/acetone mixture. This crude reaction product is purified on a column of Amberlite XAD1600, or similar resin, developing with mixtures or gradients of water/acetone. The product containing fractions are collected and evaporated to dryness, yielding the desired DTPA-$T_3S$ monoamide.

Lanthanide complexation is obtained according to known procedures by adding an equimolar amount of a lanthanide salt to the monoamide water solution and adjusting the pH at 7 with a suitable base (e.g. NaOH). Optionally, the lanthanide chelated product can be desalted by adsorption on a resin column (e.g. Amberlite XAD1600) and elution with water/solvent mixtures.

Also in this case, a sensitivity comparable to the RIA test (see Chopra et al., ibidem) is obtained and the use of radioactive isotopes avoided this represents a clear advantage over the prior art.

According to a further embodiment, the invention comprises a kit for $T_3S$ administration and dosage in serum, wherein said kit comprises an administration/therapeutic kit with a number of $T_3S$ or $T_3S$ and $T_4$ composition daily doses (i.e. the weekly, bi-weekly, monthly or bi-monthly need), preferably in the form of tablets as described above, and a dosage kit for $T_3S$ immunodetection by a non-radioactive assay.

A further preferred embodiment of the kit comprises tablets with both active principles and a kit for $T_3S$ immunodetection in serum. In a preferred embodiment the immunodetection is an ELISA test as described above.

Figure 2:
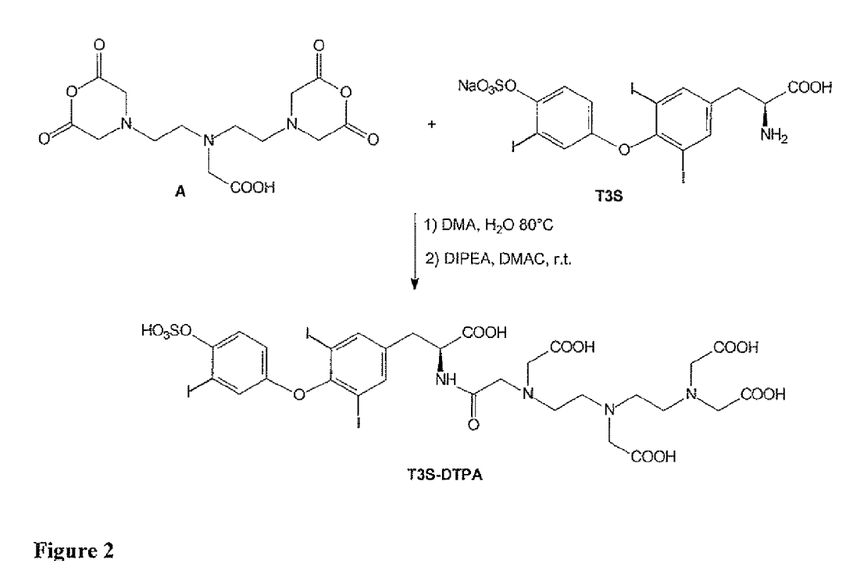
FIG. 2. Schematic of DTPA-$T_3S$ monoamide synthesis.

The kit comprises a container for a non radioactive immunoassay according to the alternative embodiments described above and container for the weekly need of the solid daily dosage described above. The container for the solid daily dosage may be formulated for the weekly, Formula II A schematic of its synthesis is shown in FIG. 2 and can be summarized as follows: DTPA dianhydride is partially hydrolysed by adding an approximately equimolar amount of water dissolved in a suitable organic solvent, then the product, mainly composed of DTPA monoanhydride is reacted with $T_3S$, in presence of a suitable organic or inorganic base. After solvent evaporation, the oily residue is diluted with water. The resulting precipitate is collected, bimonthly, monthly or even multiple months needs, according to the patients and therapeutic treatment need.

EXPERIMENTAL SECTION

As an example, absolutely non-limiting for the skilled technician, $T_3S$ may be administered for oral use at doses ranging from 1 to 1000 μg, preferably from 2.5 to 500 μg, more preferably from 5 to 250 μg.

Analogously, when in association with $T_4$, preferred doses range from 2.5-500 µg of $T_3S$ and 1 to 800 µg, $T_4$ or, even more preferably: $T_3S$: 5-250 µg and $T_4$: 5-400 µg, or $T_3S$: 10-100 µg and $T_4$ 10-200 µg.

Two representative formulations for oral administration, selected among the preferred ones, are hereinafter enclosed by way of an example. Obviously, said formulations have no limiting effect on the other possible variations, which may also comprise different types of administration, different doses or different components depending on the specific pharmacological application or the particular pathology.

Example A

Oral Formulation Containing $T_3S$

| | |
|---|---|
| $T_3S$ | 50 µg; |
| Calcium phosphate dibasic anhydrous | 103.5 mg; |
| Mais starch | 17.65 mg; |
| Microcrystalline cellulose | 5 mg; |
| Sodium carboxymethylamide | 5 mg; |
| Talc | 5 mg; |
| Citric acid | 2.8 mg; |
| Magnesium stearate | 1 mg |

Example B

Oral Formulation Containing $T_3S$ and $T_4$

| | |
|---|---|
| $T_3S$ | 50 µg; |
| $T_4$ sodium salt | 125 µg; |
| Calcium phosphate dibasic anhydrous | 103.5 mg; |
| Mais starch | 17.525 mg; |
| Microcrystalline cellulose | 5 mg; |
| Sodium carboxymethylamide | 5 mg; |
| Talc | 5 mg; |
| Citric acid | 2.8 mg; |
| Magnesium stearate | 1 mg |

Example C

Tablets Comprising $T_3S$

Pre Mixture

In a 2-L amber glass of mixer Turbola transfer a portion Avicel PH102 and a $T_3S$ salt and mix for 5'±15".

Final Mixture

In a stainless steel tank of double cone mixer, transfer the pre-mixture a second portion of Avicel PH102. Mix for 10 minutes at 10 RPM.

The mix was sieved in 1-mm opening sieve and the remaining excipients: Compritol 888 ATO, Syloid 244, Acdisol, Magnesium stearate and Socal S2V DC and the last portion of Avicel PH102 were added directly in the double cone mixer, with mixing for 20 minutes at 10 rpm.

The mixture was pressed in 110-mg tablets by a rotary tabletting machine equipped with 7-mm diameter, round, flat jewls, with one-sided break-mark in the middle.

Tablets were shown to have chemical and physical characteristics according to ICH Guidelines.

Tablets were prepared and have shown to have the following characteristics:

| 20 µg dosage (25° C./60%) | | |
|---|---|---|
| Dissolution test | ≥75% after 45' | $t_0$ = 104.8%; $t_{3\ mesi}$ = 103.5%; $t_{6\ mesi}$ = 103% |
| Moisture content | ≤10% | |
| Resistence to crushing | ≥20N | |
| HPLC Title T3S | 90-110% | |
| HPLC Title T4 | 90-110% | |

| 100 µg dosage (25° C./60%) | | |
|---|---|---|
| Dissolution test | ≥75% after 45' | $t_0$ = 94.4%; $t_{3\ mesi}$ = 94.2%; $t_{6\ mesi}$ = 94.3% |
| Moisture content | ≤10% | |
| Resistence to crushing | ≥20N | |
| HPLC Title T3S | 90-110% | |
| HPLC Title T4 | 90-110% | |

Stability tests were carried out demonstrating that tablets are stable for at least 24 months.

Example D

Quantitation of $T_3S$ by Immunoassay with Chemiluminescence Detection

Synthesis of $T_3S$ Biotin Derivative

Briefly, $T_3S$ biotin derivative was synthesized as follows: N-hydroxysuccinimidyl d-biotin-15-amido-4,7,10,13-tetraoxapentadecylate A (50 mg; 0.0849 mmol) was solubilized in DMAC (2 mL), to which DIPEA (14.5 uL; 0.0866 mmol) was added, while maintaining the reaction mixture under continuous stirring at 0° C. $T_3 5$ (68.4 mg; 0.0908 mmol, prepared as described in Mol & Visser, Endocrinology 1985, 117:1-7) was then added and after a few minutes the suspension was left to heat up to room temperature to give a clear solution. It was allowed to stir for 2 h, then kept overnight at the same temperature. DMAC was evaporated under reduced pressure (10 mbar; 40° C.) to give a colourless oil. The crude so obtained was dissolved in $H_2O$ and purified by Semi-preparative HPLC. The fractions containing the product were collected, concentrated and finally lyophilized to give $T_3S$-biotin as a white solid (59.6 mg; 0.0495 mmol). Yield 58%.

A polyclonal anti-$T_3S$ antiserum was obtained in rabbits as described in Chopra et al., J. Clin. Endocrinol. Metab., 1992, 75: 189-194.

The assay was based on a competitive ELISA in which increasing amounts of $T_3S$ competed for the antibody binding with a fixed amount of $T_3S$ conjugated with biotin, in a white 96 well plate. The employment of the biotin-avidin interaction, which allows signal amplification, combined with luminescence as technique for signal development allowed for a sensibility comparable to the RIA test (described in Chopra et al., J. Clin. Endocrinol. Metab., 1992, 75: 189-194).

Standard solutions of $T_3S$ were prepared at the following concentrations: 1000, 200, 40, 8, 1.6 pg/mL in Diluent Buffer: PBS, 0.05% Tween, 0.3% BSA The tracer solution ($T_3S$-Biotin, 180.6 µM) was prepared in the above diluent buffer. Antibody solution: $T_3S$ rabbit antiserum was diluted 1:50000 in Diluent Buffer plus 8 mM ANS, 1.2 mg/mL Sodium Salicylate.

A 96 well white plate was coated over night at 4° C. with 100 µL/well of 2 µg/mL anti Rabbit IgG diluted in phosphate buffer pH 7.8. At the same time, Standard solutions of biotin labelled $T_3S$ were combined with the diluted antiserum and the $T_3S$-biotin solution as reported in Table A. The mixed samples were incubated at room temperature in the dark, over night.

The day after, the plate was washed four times with Washing Buffer (0.05% Tween 20 in PBS), then incubated in Blocking Buffer (2% BSA in Washing Buffer) for 1 h at room temperature.

Afterwards, the plate was rinsed four times with Washing Buffer, 100 μL/well of the mixed samples were added in triplicate and the plate was incubated 3 h at room temperature.

Then, the plate was rinsed three times with Washing Buffer and incubated with Streptavidin Poly-HRP (10 ng/mL in RASA, 100 μL/well) for 1 h at room temperature.

After additional six washes, the plate was incubated with SuperSignal ELISA Femto Maximum Sensitivity Substrate (100 μL/well) for 5 min in the dark and the emitted light was read as counts per second (CPS) with a luminescence plate reader

TABLE A

Calibration Curve Preparation

| | T3S/1 (μL) | T3S/1 Antiserum (μL) | T3S-biotin (μL) |
|---|---|---|---|
| CS 5 (1000 pg/mL) | 250 | 125 | 50 |
| CS 4 (200 pg/mL) | 250 | 125 | 50 |
| CS 3 (40 pg/mL) | 250 | 125 | 50 |
| CS 2 (8 pg/mL) | 250 | 125 | 50 |
| CS 1 (1.6 pg/mL) | 250 | 125 | 50 |
| B0 | — | 125 | 50 |
| NSB | — | — | 50 |

Figure 1:
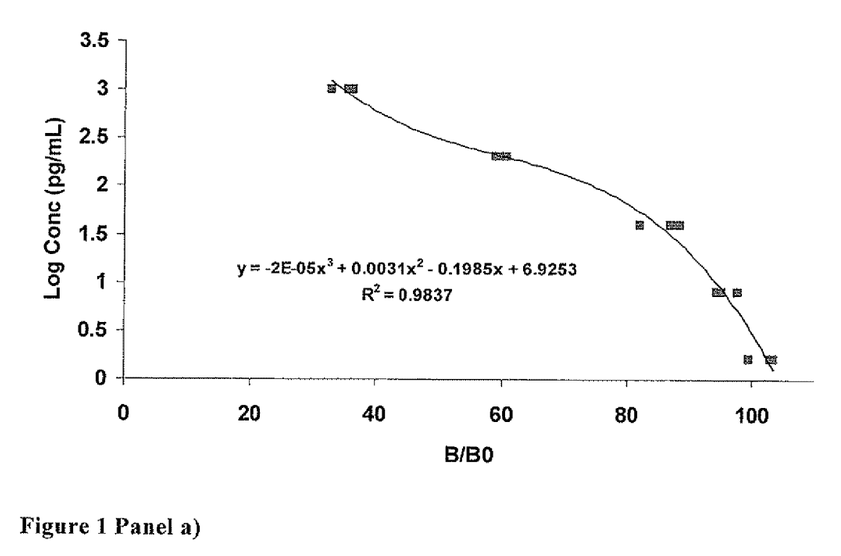
FIG. 1. Panel a) $T_3S$ calibration curve by competitive ELISA; Panel b) DELFIA calibration curve. $T_3S$ was assayed at 33.6, 56, 93.3, 155.5, 259, 432, 720, 1200, 2000 μg/mL.

The calibration curve was prepared in buffer using five concentrations of the test item in the range 1.6-1000 pg/mL. The curve is shown in FIG. 1, panel a).

Example E

Quantitation of $T_3S$ by DELFIA®

Preparation of: [[3,5-Diiodo-N-[[(carboxymethyl)[2-[(carboxymethyl)[2-[bis(carboxymethyl) amino] ethyl]amino]ethyl]amino]acetyl]-O-[3-iodo-4-(sulfooxy)phenyl]-L-tyrosinate(6-)]europate(3-)] trisodium (Formula II)

shown in FIG. 2. A solution of $H_2O$ (0.282 ml; 15.64 mmol) in DMAC (43 mL) was added dropwise to a suspension of N,N-bis[2-(2,6-dioxylenol orange-4-morpholinyl)ethyl]glycine A (4.27 g; 11.94 mmol) in DMAC (85 mL) at room temperature. At the end of the addition the mixture was heated to 80° C. After 4.5 h the reaction mixture was cooled to 25° C. and a solution of $T_3S/1$ (3 g; 3.98 mmol) and DIPEA (2.71 mL; 15.92 mmol) in DMAC (85 mL) was added dropwise over 20 min. DMAC was evaporated under reduced pressure (10 mbar; 40° C.). The oily residue was diluted with $H_2O$ (200 mL), obtaining precipitation of a yellowish solid that was filtered washed with $H_2O$ and dried. The crude so obtained was dissolved in Acetone/$H_2O$ 20:80 (v/v), the solution (pH=2.97) was loaded on an Amberlite® XAD-1600 resin column (200 mL; diam. 6 cm) and eluted with a Acetone/$H_2O$ gradient. The fractions containing the product having similar composition were collected and evaporated to give the ligand DTPA-$T_3S$ as a solid (1.27 g; 1.15 mmol). Yield 26%.

Europium chloride hexahydrate (0.17 g, 0.46 mmol) was added in portions to a solution of the ligand DTPA-$T_3S$ (0.51 g; 0.46 mmol) in $H_2O$ (50 mL) at 20° C. (pH 2.93); after each addition the suspension was stirred until complete dissolution. Once the complexation was complete the pH was adjusted to 7 with 0.1 N NaOH and the solution was desalted by elution with water/acetone from a column of Amberlite® XAD-1600 resin (100 mL; diam. 3 cm). The fractions containing the desired product and free from salts were collected and evaporated to give the compound of Formula I (0.37 g, 0.28 mmol) a yellow solid. Yield: 61%.

The immunoassay method and solutions were as described in the Example D, with the following exceptions: a DELFIA® Wash (Perkin Elmer) was used instead of the above Washing buffer. The Tracer stock solution contained the Europium 100 μM and it was stored at +4° C., protected from light. Just before use it was diluted 1:300000 in Assay Buffer to obtain a final concentration of 440 pg/mL.

The assay was performed in Delfia Yellow plates (Perkin Elmer).

After the 3-h incubation with the mixed samples, the Formula II diluted compound solution was added (50 μL per well) to all wells. The plates were then sealed with plastic adhesive sheets and incubated under agitation for 1 h at 37° C.

Synthesis of Eu-DTPA-$T_3S$ Monoamide

The reaction scheme of the synthesis of 3,5-Diiodo-N-[[(carboxymethyl)[2-[(carboxymethyl) [2-[bis(carboxymethyl)amino]ethyl]amino]ethyl]amino]acetyl]-O-[3-iodo-4-(sulfooxy)phenyl]-L-tyrosine (DTPA-$T_3S$ monoamide) is After three washes, the plates were tapped dry on absorbent paper, and Delfia Enhancement Solution (Perkin Elmer) was added (200 μL) After 1 h at 25° C., the plates were read in a Victor3 instrument according to the "Europium" manufacturer protocol.

A calibration curve was prepared using nine concentrations of the test item in the range 30-2000 pg/mL. The curve is shown in FIG. 1, panel b).

Example F

Clinical Trial

1) Ethical Issues

This study was conducted in Pisa, Italy under the guidelines provided in the Declaration of Helsinki, ICH E6 Guideline for Good Clinical Practice, and the requirements of the European Directive 2001/20/EC, and Law Decree Jun. 24, 2003, n. 211 implementing Directive 2001/20/CE in Italy, as well as the European Commission Directive 2005/28/EC of 8 Apr. 2005, laying down principles and detailed guidelines for good clinical practice for investigational medicinal products for human use, as well as the requirements for authorisation of the manufacturing or importation of such products, and related guidance.

2) Safety

The study was designed to guarantee that plasma levels of total $T_3$ could not exceed 196.6 ng/dl, the level obtained by the administration of the consolidated standard therapy of 20 μg $T_3$.

3) Protocol

About 30 human subjects with surgically excised thyroids were administered a to single dose of an oral $T_3S$ composition of the invention containing 20, 40, 80 or 160 μg $T_3S$ in tablet form. Serum levels of thyroid hormone including $T_3S$ and triiodothyronine ("$T_3$") as both free $T_3$ ("$FT_3$") and total $T_3$ ("$TT_3$") were assessed by $T_3S$ RIA, as described in Chopra et al., J. Clin. Endocrinol. Metab., 1992, 75: 189-194.

Forty eight hours prior to administration of the oral $T_3S$ composition of the invention, patients were screened for the study criteria and informed consent was requested and obtained. Twenty-four hours prior to administration of the oral $T_3S$ composition of the invention the subject was examined and all specimens for laboratory tests were collected, including thyroid function tests. On the day of the administration of the oral $T_3S$ composition of the invention, a further check of the inclusion/exclusion criteria was performed and patients were given a single dose of the oral $T_3S$ composition of the invention in tablet form according to the dose group in which they were placed.

The tablet composition was as follows:

| Ingredient | Amount per Tablet |
| --- | --- |
| $T_3S$ sodium salt | 20.6 μg |
| Equivalent to $T_3S$ | 20 μg |
| Calcium carbonate | 30 mg |
| Glycerol dibehenate | 5 mg |
| Croscarmellose sodium salt | 3.5 mg |
| Hydrate colloidal silica | 2 mg |
| Magnesium stearate | 0.5 mg |
| Microcrystalline cellulose | To 110 mg |

The initial part of the study was aimed at determining the optimal dose: as none of the patients treated with the 20, 40, 80 and 160 μg doses of the oral $T_3S$ composition of the invention had serum levels of $TT_3$ exceeding 196.6 ng/dl, the 160 μg dose was selected for use in the second part of the study.

12 subjects received a single dose of the oral composition of the invention containing 160 μg $T_3S$. The absorption of $T_3S$ was assessed by measuring the serum levels of thyroid hormones $TT_3$, $FT_3$, $T_3S$, free thyroxine ("$FT_4$") and Thyrotropin (or Thyroid Stimulating hormone, "TSH").

$T_3S$ in serum was detected with a peak level two hours after administration of the oral composition, as shown in FIG. 1. In patients lacking a thyroid there is no endogenous $T_3$. Thus, all $T_3$ present in the subjects was the result of conversion of $T_3S$ from the oral compositions to $T_3$ in vivo. By monitoring serum $T_3S$ and $TT_3$ levels after administration of the oral $T_3S$ compositions, it was determined that $T_3S$ was converted to the clinically active $TT_3$ in a dose related fashion.

Serum levels of TSH and $FT_4$ were determined at 24 h and 30 minutes prior to administration, and at 24 and 48 hours±15 min after the administration of $T_3S$ composition. Gastrointestinal absorption of $T_3S$ was assessed by measurement of circulating serum concentrations of $TT_3$, $T_3S$ and $FT_3$. Circulating serum concentrations of $FT_3$ was measured pre and post dose to verify the in-vivo $T_3S$-$FT_3$ conversion in patients.

Safety and tolerability were assessed by monitoring adverse events and by monitoring effects on vital signs, ECG, hematology, blood chemistry and urinalysis after administration of the oral compositions of the invention.

4) Conclusions

Figure 3:
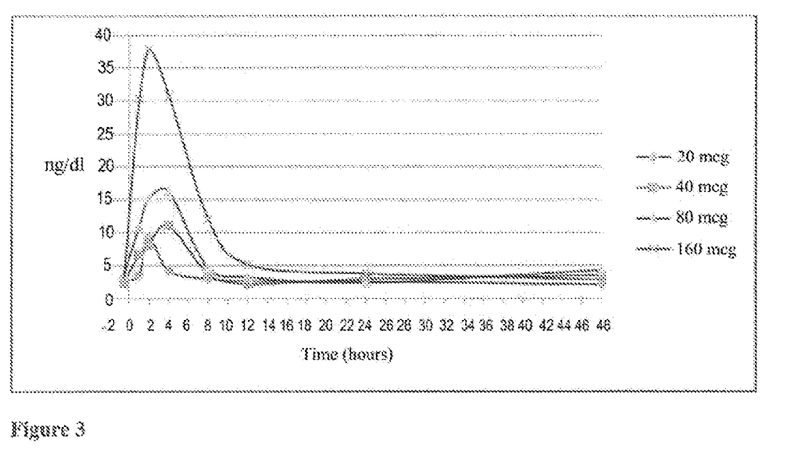
FIG. 3. Mean serum concentrations of $T_3S$ (ng/dl) levels in the four doses groups (native values).

Regardless of dose, the oral $T_3S$ compositions of the invention were found to be safe and well tolerated. The mean serum concentration of $T_3S$ (in ng/dl) for each of the four dose groups in the initial part of the study is shown in FIG. 3. For each dose group $T_3S$ was present in the serum, with a peak level two hours after oral administration. As all subjects were thyroidectomised and thus lacking endogenous $T_3S$ this data establishes that the $T_3S$ from the oral compositions of the invention crosses the gastrointestinal tract and enters the bloodstrem.

Figure 4:
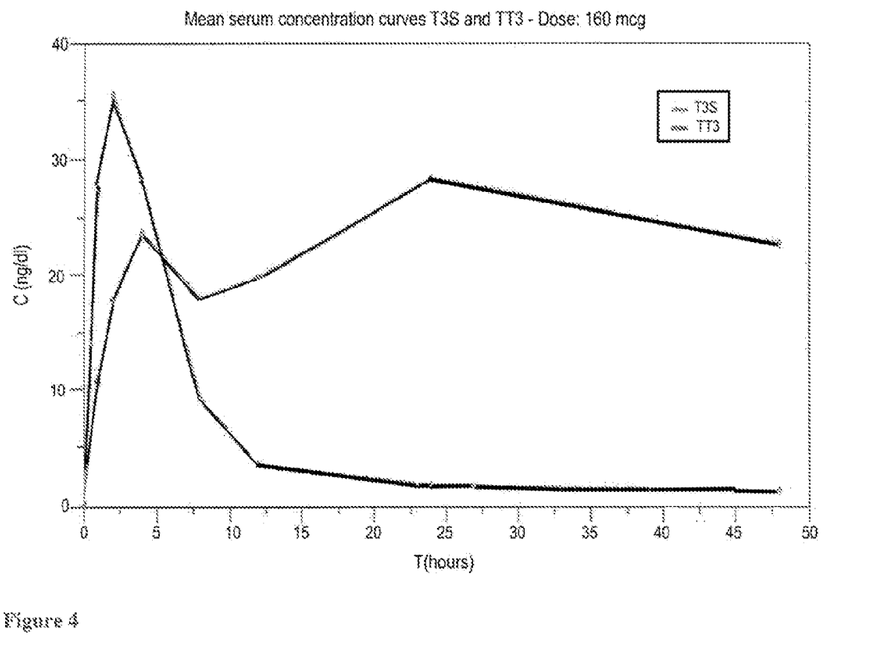
FIG. 4: Mean serum concentration curves of $T_3S$ and Total $T_3$ after administration at a dose of 160 μg.

The mean serum concentration of $T_3S$ and $TT_3$ after administration of a 160 μg dose of the oral composition of the invention is shown in FIG. 4 for a patient. $TT_3$ was detected within 4-5 hours of administration of the oral $T_3S$. As all subjects were thyroidectomised and thus lacking endogenous $T_3$, the only $T_3$ source is exogenously administered $T_3S$.

This data establishes that $T_3S$ is absorbed (i.e. it crosses the Gastrointestinal Barrier) and is found in serum after oral administration, is converted to the clinically active $T_3$ in a dose-related fashion and that $T_3$ levels in serum are still detectable 48 hrs after single dose administration.

REFERENCES

1. Chopra I J. Nature, source and relative biological significance of circulating thyroid hormones. In: Braverman L E., Utiger R D. (eds) The Thyroid, Lippincott, Philadelphia 1991, pp. 126-143.
2. Spaulding S W., Smith T J., Hinkle P M., Davis F B., Kung M P., Roth J A. Studies on the biological activity of triiodothyronine sulfate. J. Clin. Endocrinol. Metab. 1992, 74, 1062-1067.
3. Lo Presti J S., Mizuno L., Nimalysuria A., Anderson K P., Spencer C A., Nicoloff J T. Characteristics of 3,5,3'-triiodothyronine sulfate metabolism in euthyroid man. J. Clin. Endocrinol. Metab. 1991, 73, 703-709.
4. Santini F., Hurd R E., Chopra I J. A study of metabolism of deaminated and sulfoconjugated iodothyronines by rat placental iodothyronine 5-monodeiodinase. Endocrinology 1992, 131, No. 4, 1689-1694.
5. Otten M H., Mol J A., Visser T J. Sulfation proceeding deiodination of iodothyronines in rat hepatocytes. Science 1983, 221, 81-83.
6. Mol J A., Visser T J. Rapid and selective inner ring deiodination of $T_4$ sulfate by rat liver deiodinase. Endocrinology 1986, 117, 8-12.
7. Kung M P., Spaulding S W., Roth J A. Desulfation of 3,5,3'-triiodothyronine sulfate by microsomes from human and rat tissues. Endocrinology 1988, 122, 1195-1200.
8. Santini F., Chopra I J., Wu S Y., Solomon D H., Chua Teco G N. Metabolism of 3,5,3'-triiodothyronine sulfate by tissues of the fetal rat: a consideration of the role of desulfation of 3,5,3'-triiodothyronine sulfate as a source of $T_3$. Pediatr. Res. 1992, 31, 541-544.
9. De Herder W W., Hazenberg M P., Pennock-Schroeder A M., Hennemann G., Visser T J. Rapid bacteria-dependent in vitro hydrolysis of iodothyronine conjugates by intestinal contents of humans and rats. Med. Biol. 1986, 64, 31-35.
10. Santini F., Hurd R E., Lee B., Chopra I J. Thyromimetic effects of 3,5,3'-triiodothyronine sulfate in hypothyroid rats. Endocrinology 1993, 133, No. 1, 105-110.
11. Santini F., Chiovato L., Ghiri P., Lapi P., Mammoli C., Montanelli L., Scartabelli G., Ceccarini G., Coccoli L., Chopra I J., Boldrini A., Pinchera A. Serum iodothyronines in human fetus and the newborn: evidence for an important role of placenta in fetal thyroid hormone homeostasis. J. Cl. Endocrinol. Metab. 1999, 84, No. 2, 493-498.
12. Santini F., Pinchera A., Ceccarini G., Castagna M., Rosellini V., Mammoli C., Montanelli L., Zucchi V., Chopra I J., Chiovato L. Evidence for the role of the type III-iodothyronine deiodinase in the regulation of 3,5,3'-triiodothyronine content in the human central nervous system. Eur. J. Endocrinol. 2001, 144, 577-583.
13. Santini F., Cortellazzi D., Baggiani A M., Marconi A M., Beck-Peccoz P., Chopra I J. A study of the serum 3,5,3'-triiodothyronine sulfate concentration in to normal and hypothyroid fetuses at various gestational stages. J. Cl. Endocrinol. Metab. 1993, 76, No. 6, 1583-1587.
14. Chopra I J., Nguyen D. Demonstration of thyromimetic effects of 3,5,3'-triiodothyronine sulfate ($T_3S$) in Euthyroid rats. Thyroid 1996, 6, No. 3, 229-232.

EMBODIMENTS OF THE INVENTION

1. Triiodothyronine sulfate for use as a medicament.
2. Triiodothyronine sulphate for use as a medicament according to embodiment 1, having thyromimetic activity.
3. Triiodothyronine sulfate according to embodiment 2, for use in the treatment of pathologies due to organic deficiency of triiodothyronine.
4. Triiodothyronine sulfate according to embodiment 3, wherein said pathologies comprise original hypothyroidism from autoimmune thyroid affections, hormonal production defects, thyroidectomy, congenital hypothyroidism.
5. Triiodothyronine sulfate according to embodiment 2, for use in the treatment of disorders due to reduced activity of type I 5'-iodothyronine monodeiodinase.
6. Triiodothyronine sulfate according to embodiment 5, wherein said reduced activity of type I 5'-iodothyronine monodeiodinase comprises, among its grounds, hypothyroidism, non thyroidal systemic illnesses, fast, selenium shortage.
7. Pharmaceutical compositions comprising triiodothyronine sulfate as an active principle.
8. Pharmaceutical compositions according to embodiment 7, wherein said triiodothyronine sulfate is formulated in association with thyroxine.
9. Pharmaceutical compositions according to embodiment 7 and 8, wherein said compositions further comprise additives like excipients, diluents, dissolvents, solvents, carriers, dyestuffs, flavourings, sweeteners.
10. Pharmaceutical compositions according to embodiment 7, wherein triiodothyronine sulfate is administered at doses raging from 5 to 1000 µg.
11. Pharmaceutical compositions according to embodiment 10, wherein triiodothyronine sulfate is administered at doses raging from 10 to 500 µg.
12. Pharmaceutical compositions according to embodiment 10, wherein triiodothyronine sulfate is administered at doses raging from 25 to 250 µg.
13. Pharmaceutical compositions according to embodiment 8, wherein said association is administered at doses ranging from 10 to 500 µg of triiodothyronine sulfate and from 10 to 250 µg of thyroxine.
14. Pharmaceutical compositions according to embodiment 8, wherein said association is administered at doses ranging from 25 to 250 µg of triiodothyronine sulfate and from 25 to 200 µg of thyroxine.
15. Kit for the differential or sequential administration of the pharmaceutical compositions according to embodiments 8, 9 and 11 to 14.
16. Use of triiodothyronine sulfate for the preparation of the pharmaceutical compositions according to embodiments 7 to 15.

What is claimed is:

1. A stable solid oral dosage composition comprising $T_3S$ as the active principle, in a quantity ranging from 1 to 1000 µg further comprising:
    a) a diluent present at an amount from 50% to 99.99% by weight consisting of:
        at least one alkaline inorganic salt selected from the group consisting of: trisodium phosphate, tri-calcium phosphate, calcium sulphate, calcium carbonate and magnesium carbonate, wherein said alkaline inorganic salt is present at an amount up to 35% of the total diluent w/w and
        microcrystalline cellulose of the alpha type;
    b) at least one disintegrant selected from the group consisting of: croscarmellose or salts thereof, crospovidone or salts thereof, polymethacrylates and maltodextrin or salts thereof;
    c) at least one glidant selected from the group consisting of: glycerol dibehenate silica derivatives, talc, and magnesium trisilicate; and
    d) at least one lubricant selected from the group consisting of silicates, hydrate silicon dioxide, hydrate colloidal silica; magnesium stearate; and zinc stearate.
2. The solid dosage of claim 1 wherein the alkaline inorganic salt is calcium carbonate or magnesium carbonate.
3. The solid dosage of claim 2 wherein the alkaline inorganic salt is calcium carbonate.
4. The solid dosage of claim 1 wherein the disintegrant is croscarmellose or salts thereof.
5. The solid dosage of claim 1 wherein the glidant is glycerol dibehenate.
6. The solid dosage of claim 1 wherein the glidant is glycerol dibehenate, the disintegrant is croscarmellose sodium salt, and the lubricant is hydrate colloidal silica and magnesium stearate.

7. The solid dosage of claim 1 in the form of a tablet.

8. The solid dosage of claim 1 wherein $T_3S$ is in a quantity from 2.5 to 500 μg.

9. The solid dosage of claim 8 comprising $T_3S$ in a range from 5-250 μg.

10. The solid dosage of claim 9 further comprising $T_4$ in a quantity from 5-400 μg.

11. The solid dosage of claim 1 administered as a daily dose.

12. A stable solid oral dosage 80-150 mg tablet comprising $T_3S$ as the active principle, in a quantity ranging from 1 to 1000 μg further comprising:
   a) a diluent present at an amount from 50% to 99.99% by weight consisting of: 20-40 mg calcium carbonate present at an amount up to 35% of the total w/w and less than or equal to 110 mg microcrystalline cellulose of the alpha type;
   b) 2-15 mg of Glycerol dibehenate;
   c) 1-10 mg of Croscarmellose sodium salt;
   d) 0.1-5 mg of Hydrate colloidal silica; and
   e) 0.01-2 mg of Magnesium stearate.

13. The solid dosage of any one of claim 1 or 12 further comprising $T_4$ (thyroxine).

14. The stable solid or dosage of claim 12 wherein the amount of Calcium carbonate is 25-35 mg, the amount of Glycerol dibehenate is 4-8 mg, the amount of Croscarmellose sodium salt is 2-6 mg, the amount of Hydrate colloidal silica is 0.5-4 mg, and the amount of Magnesium stearate is 0.1-1 mg.

15. A kit comprising a container for a solid oral dosage composition according to claim 1 and, optionally, a container for a non-radioactive immunoassay for $T_3S$ quantitation comprising a non radioactive $T_3S$-conjugate.

16. A therapeutic or prophylactic treatment method for a hypothyroid condition due to total thyroid hormone depletion before $^{131}I$ radiotherapy comprising administering a composition according to claim to a thyroidectomised patient as the sole thyroid hormone replacement up to 5 days before administration of a radioactive isotope to said patient.

17. The therapeutic treatment method of claim 16 wherein said hypothyroid condition is selected from the group consisting of: asthenia, fatigue, skin dryness, somnolence, speech fluency impairment, cold intolerance, weight gain and memory deficit.

18. A therapeutic treatment method for a hypothyroid condition comprising administering a composition according to claim 1.

19. The therapeutic treatment method of claim 18 wherein said hypothyroid condition is selected from the group consisting of: asthenia, fatigue, skin dryness, somnolence, speech fluency impairment, cold intolerance, weight gain and memory deficit.

* * * * *